United States Patent [19]

Remers et al.

[11] Patent Number: 4,888,341
[45] Date of Patent: Dec. 19, 1989

[54] 6-SUBSTITUTED MITOMYCIN ANALOGS

[75] Inventors: William A. Remers; Salah M. Sami, both of Tucson, Ariz.

[73] Assignee: University Patents, Inc., Westport, Conn.

[21] Appl. No.: 647,055

[22] Filed: Sep. 4, 1984

[51] Int. Cl.[4] .................. C07D 487/14; A61K 31/40
[52] U.S. Cl. .................................. 514/410; 548/422
[58] Field of Search ........................ 548/422; 514/410

[56] References Cited

U.S. PATENT DOCUMENTS

| 4,746,746 | 5/1988 | Remers | 548/422 |
| 4,803,212 | 2/1989 | Vyas et al. | 514/410 |
| 4,814,445 | 3/1989 | Vyas et al. | 548/422 |

FOREIGN PATENT DOCUMENTS

| 770128 | 10/1967 | Canada | 548/422 |
| 770608 | 10/1967 | Canada | 548/422 |
| 42-022378 | 11/1967 | Japan | 548/422 |

OTHER PUBLICATIONS

Kyowa, *Chemical Abstracts,* vol. 97, (1982), entry 55585c.

Urakawa, *Chemical Abstracts,* vol. 94, (1981), entry 30598j.

*Primary Examiner*—Donald G. Daus
*Attorney, Agent, or Firm*—Marshall, O'Toole, Gerstein, Murray & Bicknell

[57] ABSTRACT

Novel methods for treatment of neoplastic disease states in animals, which methods comprise administering a therapeutically effective amount of a compound of the formula IV,

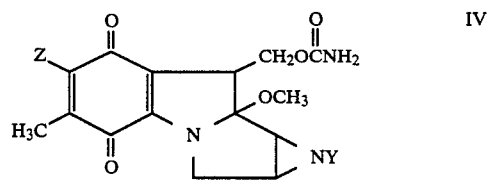

wherein: Y is hydrogen or lower alkyl; and Z is a radical of the formula —O—R, wherein R is:
a substituted lower alkyl radical selected from the group consisting of mono- and di-hydroxy lower alkyl, cyano lower alkyl, halo lower alkyl, lower alkyl amino lower alkyl, hydroxy lower alkylthio lower alkyl, hydroxy lower alkyldithio lower alkyl, di-lower alkoxy lower alkyl, hydroxy or lower alkoxy substituted lower alkoxy lower alkyl, and cyclo lower alkyl substituted lower alkyl; or
a lower alkenyl radical; or
a lower alkynyl radical; or
a substituted or unsubstituted oxygen-containing heterocyclic radical selected from the group consisting of tetrahydro furanyl or lower alkyl substituted derivatives thereof, lower alkyl substituted oxiranyl, lower alkyl substituted dioxolanyl, lower alkyl substituted pyranyl, or lower alkyl substituted furanyl.

3 Claims, No Drawings

6-SUBSTITUTED MITOMYCIN ANALOGS

BACKGROUND

The present invention relates generally to antibiotic mitosane compounds and to their use in the treatment of neoplastic disease states in animals.

The disclosures of my U.S. Pat. Nos. 4,268,676 and 4,460,599; my co-pending U.S. patent application Ser. No. 264,187 filed May 15, 1981; and my co-pending U.S. patent application Ser. No. 464,612 filed Feb. 7, 1983, are specifically incorporated by reference herein to the extent that they may provide essential and nonessential material relating to the present invention.

Briefly summarized, said U.S. Pat. Nos. 4,268,676 and 4,460,599 set forth a statement of the background of the ongoing search in the art for new and useful compounds which are structurally related to the mitomycins, which possess antibiotic activity, which have low toxicity and which display a substantial degree of antitumor activity in animals. More particularly, they disclose new compounds of the formula I,

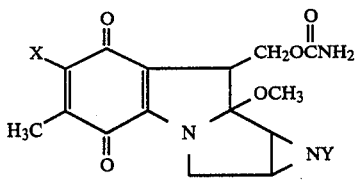

wherein: Y is hydrogen or lower alkyl; and X is a thiazolamino radical, a furfurylamino radical or a radical of the formula,

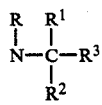

in which R, $R^1$ and $R^2$ are the same or different and selected from the group consisting of hydrogen and lower alkyl, and $R^3$ is selected from the group consisting of lower alkenyl, halo-lower alkenyl, lower alkynyl, lower alkoxycarbonyl, thienyl, formamyl, tetrahydrofuryl and benzene sulfonamide.

Said U.S. patents also disclose novel methods for treatment of neoplastic disease states in animals, which methods comprise administering a therapeutically effective amount of a compound of the formula Ia,

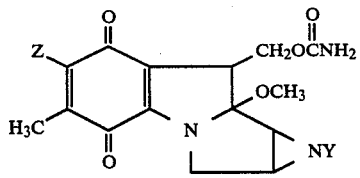

wherein: Y is hydrogen or lower alkyl; and Z is a thiazolamino radical, a furfurylamino radical, a cyclopropylamino radical, a pyridylamino radical, or a radical of the formula,

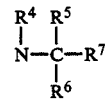

in which $R^4$, $R^5$, and $R^6$ are the same or different and selected from the group consisting of hydrogen and lower alkyl, and $R^7$ is selected from the group consisting of lower alkenyl, halo-lower alkenyl, lower alkynyl, lower alkoxy-carbonyl, halo-lower alkyl, hydroxy-lower alkyl, pyridyl, thienyl, formamyl, tetrahydrofuryl, benzyl, and benzene sulfonamide.

Co-pending U.S. patent application Ser. No. 264,187 also discloses compounds with a substantial degree of antitumor activity in animals of the following formula IIa,

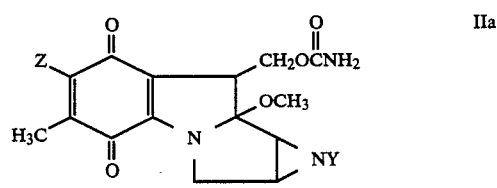

wherein: Y is hydrogen or lower alkyl; and Z is a lower alkoxy substituted quinolinylamino radical, a cyano substituted pyrazolylamino radical or a mono- or di-lower alkyl substituted thiazolamino radical, or a nitrogen-containing heterocyclic radical selected from the group consisting of 1-pyrrolinyl, 1-indolinyl, N-thiazolidinyl, N-morpholinyl, 1-piperazinyl, and N-thiomorpholinyl radicals, or a cyano, phenyl, carboxamido or lower alkoxycarbonyl substituted 1-aziridinyl radical, or a lower alkyl, formyl or acetylphenyl substituted 1-piperazinyl radical, or an hydroxy or piperidyl substituted 1-piperidyl radical, or a lower alkoxy, amino or halo substituted pyridylamino radical, or a carboxamido, mercapto or methylenedioxy substituted anilino radical, or a radical of the formula,

wherein R is hydrogen or lower alkyl and R' is a nitrogen-containing heterocyclic radical selected from the group consisting of quinuclidinyl, pyrazolyl, 1-triazolyl, isoquinolinyl, indazolyl, benzoxazolyl, thiadiazolyl and benzothiadiazolyl, and lower alkyl and halo substituted derivatives thereof, or a butyrolactonyl radical, or an adamantyl radical, or a mono-lower alkoxy substituted phenyl radical, or a substituted lower alkyl radical selected from the group consisting of mercapto lower alkyl, carboxy lower alkyl, mono-, di- and tri-lower alkoxy lower alkyl, lower alkyl thio lower alkyl and lower alkoxycarbonyl substituted derivatives thereof, cyano lower alkyl, mono-, di- and tri-lower alkoxy phenyl lower alkyl, phenyl cyclo lower alkyl, 1-pyrrolidinyl lower alkyl, N-lower alkyl pyrrolidinyl lower alkyl, N-morpholinyl lower alkyl, and lower dialkylamino lower alkyl.

Co-pending U.S. patent application Ser. No. 464,612 also discloses compounds for use in treatment of neoplastic disease states in animals of the formula IIIa,

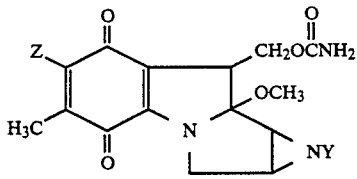

wherein: Y is hydrogen or lower alkyl; and Z is an hydroxy substituted 1-pyrrolidinyl radical, or a lower alkyl substituted piperidyl radical, or a 1-piperazinyl radical or an acetamino, acetyl, carbamido, cyano, carboxy lower alkylamino, di-lower alkoxy, nitro, sulfamyl, or lower alkyl substituted anilino radical, or a radical of the formula,

wherein R is hydrogen or lower alkyl and $R^1$ is a nitrogen containing heterocyclic radical selected from the group consisting of amino substituted triazolyl, lower alkyl substituted isothiazolyl, benzothiazolyl, and nitro and halo substituted derivatives of benzothiazolyl, or $R^1$ is a substituted lower alkyl radical selected from the group consisting of amino lower alkyl, lower alkylamino lower alkyl, hydroxy lower alkylamino lower alkyl, hydroxy lower alkoxy lower alkyl, imidazolyl lower alkyl, nitro substituted imidazolyl lower alkyl, mono- and di-hydroxy phenyl lower alkyl, nitro substituted pyridylamino lower alkyl, piperazinyl lower alkyl, and pyridyl ethyl.

The synthesis and biological evaluation of a series of 7-alkoxymitosanes including 7-ethoxy, 7-n-propoxy, 7-i-propoxy, 7-n-butoxy, 7-i-butoxy, 7-sec-butoxy, 7-n-amyloxy, 7-i-amyloxy, 7-n-hexyloxy, 7-cyclohexyloxy, 7-n-heptyloxy, 7-n-octyloxy, 7-n-decyloxy, 7-stearyloxy, 7-(2-methoxy)ethoxy, and 7-benzyloxy derivatives of mitomycin A was reported in Urakawa, C., et al., *J. Antibiotics*, 33: 804–809 (1980). Also shown is the 7-i-propoxy derivative of mitomycin B. Most of these compounds displayed antibacterial activities against Gram-positive and Gram-negative bacterial strains and strong inhibition of growth of HeLa S-3 cells in vitro.

Also pertinent to the background of the present invention are the following references: Cosulich, et al., U.S. Pat. No. 3,332,944; Matsui, et al., U.S. Pat. No. 3,410,867; Nakano, et al., U.S. Pat. No. 4,231,936; Matsui, et al., U.S. Pat. No. 3,429,894; Remers, U.S. Pat. No. 4,268,676; Matsui, et al., U.S. Pat. No. 3,450,705; Matsui, et al., U.S. Pat. No. 3,514,452; and Imai, et al., Gann, 71: 560–562 (1980).

BRIEF SUMMARY

According to the present invention, there are provided novel compounds of the formula, IV,

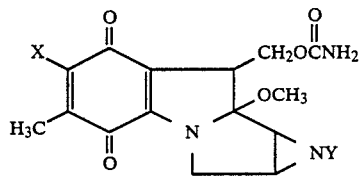

wherein: Y is hydrogen or lower alkyl; and X is a radical of the formula —O—R, wherein R is:

a substituted lower alkyl radical selected from the group consisting of mono- and di-hydroxy lower alkyl, cyano lower alkyl, halo lower alkyl, lower alkyl amino lower alkyl, hydroxy lower alkylthio lower alkyl, hydroxy lower alkyldithio lower alkyl, di-lower alkoxy lower alkyl, hydroxy or lower alkoxy substituted lower alkoxy lower alkyl, and cyclo lower alkyl substituted lower alkyl; or a lower alkenyl radical; or a lower alkynyl radical; or a substituted or unsubstituted oxygen-containing heterocyclic radical selected from the group consisting of tetrahydro furanyl or lower alkyl substituted derivatives thereof, lower alkyl substituted oxiranyl, lower alkyl substituted dioxolanyl, lower alkyl substituted pyranyl, or lower alkyl substituted furfuryl.

Also provided according to the invention are novel methods for treatment of neoplastic disease states in animals, which methods comprise administering a therapeutically effective amount of a compound of the formula, IV.

Unless otherwise indicated, the term "lower", applied to "alkoxy" radicals shall designate such straight or branched chain radicals as to include from one to eight carbon atoms. By way of illustration, "lower alkoxy" shall mean and include methoxy, ethoxy, propoxy, butoxy, pentoxy, hexoxy, heptoxy and octoxy radicals as well as isopropoxy radicals, t-butoxy radicals and the like. Similarly, "lower", as applied to "alkyl", shall designate a radical having one to eight carbon atoms; and, as applied to "alkenyl" and "alkynyl", shall designate a radical having two to eight carbon atoms.

Mitomycin derivatives of the invention are prepared by the reaction of mitomycin A with the appropriately selected alcohol in the presence of potassium hydroxide compounds or by the reaction of 7-hydroxy mitosane with the appropriately selected 1-alkyl-3-aryl triazene in the presence of methylene chloride. The preparative reactions generally yield the desired product as a crystalline solid which is readily soluble in alcohol.

Therapeutic methods of the invention comprehend the administration of effective amounts of one or more of the compounds of formula IV, as an active ingredient, together with desired pharmaceutically acceptable diluents, adjuvants and carriers, to an animal suffering from a neoplastic disease state. Unit dosage forms of compounds administered according to the methods of the invention may range from about 0.001 to about 5.0 mg and preferably from about 0.004 to about 1.0 mg, of the compounds. Such unit dosage quantities may be given to provide a daily dosage of from about 0.1 to about 100 mg per kilogram, and preferably from about 0.2 to about 51.2 mg per kilogram, of body weight of the animal treated. Parenteral administration, and especially intraperitoneal administration, is the preferred route for practice of the inventive methods.

Other aspects and advantages of the present invention will become apparent upon consideration of the following description.

DETAILED DESCRIPTION OF THE INVENTION

The following Examples 1 through 21, describing preparation of certain presently preferred compounds according to the invention, are for illustrative purposes only and are not to be construed as limiting the invention. Unless otherwise indicated, all reactions were carried out at room temperature (20° C.), without added heat. Unless otherwise indicated, all thin layer chromatographic (TLC) procedures employed to check the progress of reactions involved the use of a pre-coated silica-gel plate and a mixture of acetone and chloroform (1:1 by volume) as a developing solvent.

EXAMPLE 1

1,1a,2,8,8a,8b-Hexahydro-8-(hydroxymethyl)-8a-methoxy-5-methyl-6-(allyloxy)-azirino[2',3':3,4]pyrrolo[1,2-a]indole-4,7-dione carbamate A solution of mitomycin A (100 mg or 0.286 mmole) in 4 ml of allyl alcohol was stirred at room temperature and under nitrogen for 45 minutes with 500 mg of a 1.6% solution of potassium hydroxide (KOH) in allyl alcohol. The reaction mixture was decomposed with excess dry ice while immersing the flask into a water bath at room temperature. It was then isolated on a silica gel plate using ether, which elutes the allyl alcohol to the top of the plate (the plate was developed several times), followed by $CHCl_3$-acetone 1:1 which elutes the product. This procedure gives 45 mg (42%) of the title compound, having a melting point of 106°–111° C. (decomposition) and providing the following analysis:

NMR ($CDCl_3$,TS) 'δ' values in ppm. Disappearance of a singlet at 4.02 due to the 6-methoxy group in mitomycin A and the appearance of new signals at 4.4–4.85 (m,4), 5.15–5.3 (dd,1), 5.3–5.5 (dd,1) and 5.8–6.2 (m,1).

EXAMPLE 2

1,1a,2,8,8a,8b-Hexahydro-8-(hydroxymethyl)-8a-methoxy-5-methyl-6-(propargyloxy)-azirino[2',3':3,4]pyrrolo[1,2-a]indole-4,7-dione carbamate A solution of mitomycin A (100 mg or 0.286 mmole) in 4 ml of propargyl alcohol was stirred at room temperature and under nitrogen for 45 minutes with 500 mg of a 1.6% solution of KOH in propargyl alcohol. The reaction mixture was decomposed with excess dry ice while immersing the flask into a water bath at room temperature. It was then isolated on a silica gel plate using ether, which elutes the propargyl alcohol to the top of the plate (the plate was developed several times), followed by $CHCl_3$-acetone 1:1 which elutes the product. This procedure gives 33 mg (31%) of the title compound, having a melting point of 77°–80° C. (decomposition) and providing the following analysis:

NMR ($CDCl_3$,TS) 'δ' values in ppm. Disappearance of a singlet at 4.02 (due to the 6-methoxy group in mitomycin A) and the appearance of a group of peaks at 4.5–4.9 (m,4) and a singlet at 2.5.

EXAMPLE 3

1,1a,2,8,8a,8b-Hexahydro-8-(hydroxymethyl)-8a-methoxy-5-methyl-6-(cyclobutylmethoxy)-azirino[2',3':3,4]pyrrolo[1,2-a]indole-4,7-dione carbamate A solution of mitomycin A (64 mg) in 4 ml of cyclobutane methanol was stirred at room temperature and under nitrogen for 45 minutes with 500 mg of a 1.6% solution of KOH in cyclobutane methanol. The reaction mixture was decomposed with excess dry ice while immersing the flask into a water bath at room temperature. It was then isolated on a silica gel plate using ether, which elutes the cyclobutane methanol to the top of the plate (the plate was developed several times). This procedure gives 21.5 mg (29%) of the title compound, having a melting point of 83°–88° C. (decomposition) and providing the following analysis:

NMR ($CDCl_3$,TS) 'δ' values in ppm. Disappearance of the singlet at 4.02 and the appearance of new bands at 3.9–4.4 (m,3) and 1.65–2.10 (s,7).

EXAMPLE 4

1,1a,2,8,8a,8b-Hexahydro-8-(hydroxymethyl)-8a-methoxy-5-methyl-6-{[2-(2-ethoxy)ethoxy]ethoxy}-azirino[2',3':3,4]pyrrolo[1,2-a]indole-4,7-dione carbamate A solution of mitomycin A (100 mg or 0.286 mmole) in 4 ml of diethylene glycol monoethyl ether was stirred at room temperature and under nitrogen for 45 minutes with 480 mg of a 1.6% solution of KOH in diethylene glycol monoethyl ether. The reaction mixture was decomposed with excess dry ice while immersing the flask into a water bath at room temperature. It was then isolated on a silica gel column using $CHCl_3$-MeOH 9:1 as solvent. Final purification was achieved by preparative thin layer chromatography on silica gel with a mixture of $CHCl_3$-MeOH 9:1. This procedure resulted in 80 mg (62%) of the title compound, having a melting point of 140°–143° C. (decomposition) and providing the following analysis:

NMR ($CDCl_3$,TS) 'δ' values in ppm. Disappearance of a sharp singlet at 4.02 and the appearance of peaks at 4.15 (m,2), 3.45–3.9 (m,11) and 1–1.6 (t,3).

EXAMPLE 5

1,1a,2,8,8a,8b-Hexahydro-8-(hydroxymethyl)-8a-methoxy-5-methyl-6-(tetrahydrofurfuryloxy)-azirino[2',3':3,4]pyrrolo[1,2-a]indole-4,7-dione carbamate A solution of mitomycin A (100 mg or 0.286 mmole) in 4 ml of tetrahydrofurfuryl alcohol was stirred at room temperature and under nitrogen for 45 minutes with 480 mg of a 1.6% solution of KOH in tetrahydrofurfuryl alcohol. The reaction mixture was decomposed with excess dry ice while immersing the flask into a water bath at room temperature. The product was chromatographed on a silica gel column using $CHCl_3$-MeOH 9.5:0.5 as solvent. Further purification of the product was done by preparative thin layer chromatography (silica gel, $CHCl_3$-MeOH 9.5:0.5). This procedure resulted in 72 mg (60%) of the desired product having a melting point of 128°–133° C. (decomposition) and providing the following analysis:

NMR ($CDCl_3$,TS) 'δ' values in ppm. Disappearance of a singlet at 4.02 ppm and the appearance of new peaks at 4.2–4.35 (d,2), 4.00–4.2 (m,1), 3.7–3.9 (t,2), 1.75–2.00 ppm (s,7).

EXAMPLE 6

1,1a,2,8,8a,8b-Hexahydro-8-(hydroxymethyl)-8a-methoxy-5-methyl-6-[4-(2,2-dimethyl-1,3-dioxolanyl)-methoxy]-azirino[2',3':3,4]pyrrolo[1,2-a]indole-4,7-dione carbamate A solution of mitomycin A (100 mg or 0.286 mmole) in 4 ml of 2,2-dimethyl-1,3-dioxolane was stirred at room temperature and under nitrogen for 45 minutes with 480 mg of a 1.6% solution of KOH in 2,2-dimethyl-1,3-dioxolane. The reaction mixture was decomposed with excess dry ice while immersing the flask into a water bath at room temperature. The product was first isolated on a silica gel column, then on a silica gel plate using CHCl$_3$-acetone 7:3 as solvent system in both isolations. Thus, 38 mg (30%) of the desired product was produced, having a melting point of 136°–138° C. (decomposition) and providing the following analysis:

NMR (CDCl$_3$,TS) 'δ' values in ppm. Disappearance of a singlet at 4.02 and the appearance of new peaks at 1.5 (s,6), 3.9–4.25 (m,3), and 4.25–4.6 (m,3).

EXAMPLE 7

1,1a,2,8,8a,8b-Hexahydro-8-(hydroxymethyl)-8a-methoxy-5-methyl-6-[(2-pyranyl)methoxy]-azirino[2',3':3,4]pyrrolo[1,2-a]indole-4,7-dione carbamate A solution of mitomycin A (100 mg or 0.286 mmole) in 4 ml of tetrahydropyran-2-methanol was stirred at room temperature and under nitrogen for 45 minutes with 240 mg of a 1.6% solution of KOH in tetrahydropyran-2-methanol. The reaction mixture was decomposed with excess dry ice while immersing the flask into a water bath at room temperature. The reaction mixture was chromatographed on a silica gel column using CHCl$_3$ and then CHCl$_3$-MeOH 9.5:0.5. The product was further purified by preparative thin layer chromatography (silica gel, CHCl$_3$-MeOH 9.5:0.5). Thus, there was obtained 57 mg (46%) of the desired product having a melting point of 135°–138° C. (decomposition) and providing the following analysis:

NMR (CDCl$_3$,TS) 'δ' values in ppm. Disappearance of a singlet at 4.02 and the appearance of new groups of peaks at 1.3–1.6 (s,6), 3.35–3.75 (m,4), and 3.9–4.3 (m,4).

EXAMPLE 8

1,1a,2,8,8a,8b-Hexahydro-8-(hydroxymethyl)-8a-methoxy-5-methyl-6-glycidoxy-azirino[2',3':3,4]pyrrolo[1,2-a]indole-4,7-dione carbamate A solution of mitomycin A (100 mg or 0.286 mmole) in 4 ml of glycidol was stirred at room temperature and under nitrogen for 45 minutes with 500 mg of a 1.6% solution of KOH in glycidol. The reaction mixture was decomposed with excess dry ice while immersing the flask into a water bath at room temperature. The crude reaction product was chromatographed on a silica gel column using first CHCl$_3$-MeOH 9.5:0.5, which elutes glycidol and pink by-products, and then CHCl$_3$-MeOH 9:1, which elutes the product. The product was further purified by preparative thin layer chromatography on silica gel with a mixture of CHCl$_3$ and methanol 9:1 as the solvent. Thus, there was obtained 71 mg (33%) of the desired product, which gave indefinite decomposition on heating and provided the following compound analysis:

NMR (CDCl$_3$,TS) 'δ' values in ppm. Disappearance of a sharp singlet at 4.02 and increase in the proton intensity of the group of peaks between 3.5–4.5 by 5.

EXAMPLE 9

1,1a,2,8,8a,8b-Hexahydro-8-(hydroxymethyl)-8a-methoxy-5-methyl-6-[2-(2-hydroxyethyldithio)ethoxy]azirino[2',3':3,4]pyrrolo[1,2-a]indole-4,7-dione carbamate A solution of mitomycin A (100 mg or 0.286 mmole) in 4 ml of 2-hydroxyethyldisulphide was stirred at room temperature and under nitrogen for 45 minutes with 240 mg of a 1.6% solution of KOH in 2-hydroxyethyldisulphide. The reaction mixture was decomposed with excess dry ice while immersing the flask into a water bath at room temperature. The reaction mixture was chromatographed on a silica gel column using CHCl$_3$-acetone 1:1 and the CHCl$_3$-MeOH 9:1 as solvent systems. The product was further purified by preparative thin layer chromatography on silica gel using CHCl$_3$-acetone 3:7. Thus, there was obtained 23 mg (44%) of the desired product, having a melting point of 87°–95° C. (decomposition) and providing the following analysis:

NMR (CDCl$_3$,TS) 'δ' values in ppm. The disappearance of a singlet at 4.02 and the appearance of strong absorption at 4.3–4.8 (m,4), 4.3–4 (m,3), and 2.5–(m,6).

EXAMPLE 10

1,1a,2,8,8a,8b-Hexahydro-8-(hydroxymethyl)-8a-methoxy-5-methyl-6-(2-hydroxyethoxy)-azirino[2',3':3,4]pyrrolo[1,2-a]indole-4,7-dione carbamate A solution of mitomycin A (200 mg) in 10 ml of ethylene glycol was stirred at room temperature and under nitrogen for 45 minutes with 480 mg of a 1.6% solution of KOH in ethylene glycol. The reaction mixture was decomposed with excess dry ice while immersing the flask into a water bath at room temperature. The reaction mixture was chromatographed on a column packed with neutral alumina using CHCl$_3$-MeOH 8:2 as the solvent. This process separates the reaction products which are pink in color from ethylene glycol. The product from the pink fraction was rechromatographed on a silica gel plate with acetone to give two major bands. The product obtained from the second band was rechromatographed on a silica gel plate with a mixture of chloroform and methanol 9:1 to give the desired product. This procedure gave 64 mg (29%) of the desired product, having a melting point of 72°–74° C. (decomposition) and providing the following analysis:

NMR (CDCl$_3$,TS) 'δ' values in ppm. The disappearance of a sharp singlet at 4.02 and the appearance of a band at 3.9–4.5 (m,5).

EXAMPLE 11

1,1a,2,8,8a,8b-Hexahydro-8-(hydroxymethyl)-8a-methoxy-5-methyl-6-[(3-tetrahydrofuranyl)oxy]-azirino[2',3':3,4]pyrrolo[1,2-a]indole-4,7-dione carbamate A solution of mitomycin A (100 mg or 0.286 mmole) in 4 ml of 3-hydroxy tetrahydrofuran was stirred at room temperature and under nitrogen for 45 minutes with 500 mg of a 1.6% solution of KOH in 3-hydroxy tetrahydrofuran. The reaction mixture was decomposed with excess dry ice while immersing a water bath at room temperature. The product was isolated twice on silica gel plates. In the first isolation, the solvent was ether, which elutes 3-hydroxy tetrahydrofuran while the pink product stayed on the base line. In the second isolation a mixture of chloroform and methanol 9:1 was used as solvent. This procedure resulted in 36 mg (31%) of the desired product, having a melting point of 68°–75° C. (decomposition) and providing the following analysis:

NMR (CDCl$_3$,TS) 'δ' values in ppm. The disappearance of a sharp singlet at 4.02 and the appearance of new peaks at 2.00–2.20 (m,2), 3.7–4.00 (m,4), and 5.4–5.6 (m,1).

EXAMPLE 12

1,1a,2,8,8a,8b-Hexahydro-8-(hydroxymethyl)-8a-methoxy-5-methyl-6-(3-hydroxypropoxy)-azirino[2',3':3,4]pyrrolo[1,2-a]indole-4,7-dione carbamate A solution of mitomycin A (100 mg or 0.286 mmole) in 4 ml of propane-1,3-diol was stirred at room temperature and under nitrogen for 45 minutes with 300 mg of a 1.6% solution of KOH in propane-1,3-diol. The reaction mixture was decomposed with excess dry ice while immersing the flask into a water bath at room temperature. The product was isolated on a silica gel column using 1% methanol in ether, which elutes propane-1,3-diol, followed by a mixture of chloroform and methanol 6:4, which elutes the product, as the solvent systems. The product was then isolated twice on silica gel plates. In the first isolation, the solvent was 1% methanol in ether, which elutes any contaminants of propane-1,3-diol while the product stayed on the base line. In the second isolation a mixture of chloroform and methanol 9:1 was used as the solvent.

This procedure gives 26 mg (23%) of the desired compound, having a melting point of 80°–100° C. (decomposition) and providing the following analysis:

NMR (CDCl$_3$,TS) 'δ' values in ppm. The disappearance of a singlet at 4.02 and the appearance of new peaks at 2.0–2.2 (m,2), 3.7–3.9 (t,2), and 4.25–4.45 (t,2).

EXAMPLE 13

1,1a,2,8,8a,8b-Hexahydro-8-hydroxymethyl)-8a-methoxy-5-methyl-6-[2-(2-hydroxyethoxy)ethoxy]-azirino[2',3':3,4]pyrrolo[1,2-a]indole-4,7-dione carbamate A solution of mitomycin A (79 mg) in 4 ml of 2-hydroxyethyl ether was stirred at room temperature and under nitrogen for 45 minutes with 560 mg of a 1.6% solution of KOH in 2-hydroxyethyl ether. The reaction mixture was decomposed with excess dry ice while immersing the flask into a water bath at room temperature. The reaction mixture was chromatographed on a silica gel column using 10% acetone in ether, which elutes 2-hydroxyethyl ether, and then a mixture of chloroform and methanol 6:4, which elutes the pink product, as solvent systems. The isolated product was chromatographed on a silica gel plate using 10% acetone in ether to remove any 2-hydroxyethyl ether from the product which stays on the base line. Final purification of the product was made by preparative thin layer chromatography on a silica gel plate with a mixture of chloroform and methanol 9:1.

This procedure gives 45 mg (47%) of the desired product, having a melting point of 125°–128° C. (decomposition) and providing the following analysis:

NMR (CDCl$_3$,TS) 'δ' values in ppm. The disappearance of a sharp singlet at 4.02 and the appearance of new peaks at 3.4–3.85 (m,9) and 4.4–4.7 (m,4).

EXAMPLE 14

1,1a,2,8,8a,8b-Hexahydro-8-(hydroxymethyl)-8a-methoxy-5-methyl-6-[2-(N,N-dimethylamino)ethoxy]-azirino[2',3':3,4]pyrrolo[1,2-a]indole-4,7-dione carbamate A solution of mitomycin A (200 mg) in 4 ml of N,N-dimethyl ethanolamine was stirred at room temperature and under nitrogen for 45 minutes with 480 mg of a 1.6% solution of KOH in N,N-dimethyl ethanolamine. The reaction mixture was decomposed with excess dry ice while immersing the flask into a water bath at room temperature. The crude reaction mixture was evaporated under reduced pressure. The residue was triturated with ether and the resulting solid was filtered off. This procedure produced 167 mg (71%) of crude product, which was crystallized from ether or ether-acetone (least amount of acetone) to give reddish brown crystals, having a melting point of 140°–143° C. (decomposition) and providing the following analysis:

NMR (CDCl$_3$,TS) 'δ' values in ppm. The disappearance of a singlet at 4.02 and the appearance of new peaks at 2.25 (S,6), 2.55–2.65 (t,2), and 4.33–4.45 (t,2).

EXAMPLE 15

1,1a,2,8,8a,8b-Hexahydro-8-(hydroxymethyl)-8a-methoxy-5-methyl-6-[2,2-(dimethoxy)ethoxy]-azirino[2',3':3,4]pyrrolo[1,2-a]indole-4,7-dione carbamate 3-(2,2-dimethoxy)ethyl-1-phenyltriazine was prepared as follows. A cold solution of 7.5 g of benzenediazonium hexafluorophosphate in 100 ml of N,N-dimethylformamide as added at 0° C. to a solution of 3.25 g of aminoacetaldehyde dimethylacetal in 100 ml of N,N-dimethylformamide containing excess potassium carbonate. After 2 hours the mixture was poured into ice water and extracted with hexane. This extract was dried and concentrated under reduced pressure to give 3.0 g of the desired product as a red oil.

A solution of 3 g of 2,2-dimethoxyethylphenyltriazine in 75 ml of dry methylene chloride was added to a solution of 7-hydroxy mitosane (obtained from the hydrolysis of 0.3 g of mitomycin C) in 75 ml of dry methylene chloride. The reaction mixture was stirred at room temperature under nitrogen for 48 hours. The solvent was then evaporated and the residue was purified by preparative thin layer chromatography on silica gel with a mixture of chloroform and methanol 9:1. This procedure gave 136 mg (36% based on mitomycin C) of the desired compound, having a melting point of 68°–75° C. (decomposition) and providing the following analysis:

NMR (CDCl$_3$,TS) 'δ' values in ppm. The disappearance of the peak at 4.02 and the appearance of new peaks at 3.4 (S,6), 4.25–4.3 (d,2) and 4.4–4.9 (m,5).

EXAMPLE 16

1,1a,2,8,8a,8b-Hexahydro-8-(hydroxymethyl)-8a-methoxy-5-methyl-6-(furfuryloxy)-azirino[2',3':3,4]pyrrolo[1,2-a]indole-4,7-dione carbamate 3-furfuryl-1-phenyltriazine was prepared as follows. A cold solution of 10 g of benzenediazonium hexafluorophosphate in 25 ml of N,N-dimethylformamide was added in portions at 0° C. to a mixture of 3.88 g of furfurylamine in 25 ml of N,N-dimethylformamide containing excess potassium carbonate. After 2 hours the mixture was poured into ice water. The resulting precipitate was collected and crystallized from hexane to give 1 g of the desired product as yellow needles.

A solution of 0.7 g of 3-furfuryl-1-phenyltriazine in 15 ml of dry methylene chloride was added to a solution of 7-hydroxy mitosane (obtained from the hydrolysis of 0.5 g of mitomycin C) in 15 ml of dry methylene chloride. The reaction mixture was stirred at room temperature under nitrogen for 72 hours. The solvent was then evaporated and the residue was purified by preparative thin layer chromatography on silica gel with a mixture of chloroform and methanol 9:1. The material obtained from purification on silica gel was further purified on a precoated neutral alumina plate using a mixture of chloroform and acetone as solvent. This procedure gave 16 mg (4.3%) of the desired compound, having a melting point of 110°–117° C. (decomposition) and showing the following analysis:

NMR (CDCl$_3$,TS) 'δ' values in ppm. The disappearance of the peak at 4.02 and the appearance of new peaks at 5.45 (S,2), 6.5 (s,2) and 7.4–7.55 (d,1).

EXAMPLE 17

1,1a,2,8,8a,8b-Hexahydro-8-(hydroxymethyl)-8a-methoxy-5-methyl-6-[2-(2-methoxyethoxy)ethoxy]-azirino[2',3':3,4]pyrrolo[1,2-a]indole-4,7-dione carbamate A solution of mitomycin A (100 mg) in 4 ml of 2-(2-methoxyethoxy)ethanol was stirred at room temperature and under nitrogen for 45 minutes with 240 mg of a 1.6% solution of KOH in 2-(2-methoxyethoxy)ethanol. The reaction mixture was decomposed with excess dry ice while immersing the flask into a water bath at room temperature. It was then isolated on a silica gel plate using ether, which elutes the allyl alcohol to the top of the plate (the plate was developed several times), followed by chloroform-methanol 9:1 which elutes the product. This procedure gives 72 mg (58%) of the desired compound, having a melting point of 102°–104° C. and providing the following analysis:

NMR (CDCl$_3$,TS) 'δ' values in ppm. The disappearance of a singlet at 4.02 and the appearance of new bands at 3.4 (S,3), 3.5–3.85 (m,8), and 4.35–4.55 (t,2).

EXAMPLE 18

1,1a,2,8,8a,8b-Hexahydro-8-(hydroxymethyl)-8a-methoxy-5-methyl-6-(3-chloropropoxy)-azirino[2',3':3,4]pyrrolo[1,2-a]indole-4,7-dione carbamate A solution of mitomycin A (100 mg) in 4 ml of 3-chloropropanol was stirred at room temperature and under nitrogen for 45 minutes with 240 mg of a 1.6% solution of KOH in 3-chloropropanol. The reaction mixture was decomposed with excess dry ice while immersing the flask into a water bath at room temperature. It was then isolated on a silica gel plate using ether, which elutes the allyl alcohol to the top of the plate (the plate was developed several times), followed by a mixture of chloroform-methanol 9:1 which elutes the product. This procedure gives 75 mg (64%) of the desired product, having a melting point of 142°–145° C. (decomposition) and providing the following analysis:

NMR (CDCl$_3$,TS) 'δ' values in ppm. The disappearance of a singlet at 4.02 and the appearance of new peaks at 2.15–2.25 (t,2), 3.4–3.8 (m,4) and 4.35–4.5 (t,2).

EXAMPLE 19

1,1a,2,8,8a,8b-Hexahydro-8-(hydroxymethyl)-8a-methoxy-5-methyl-6-(2-cyanoethoxy)-azirino[2',3':3,4]pyrrolo[1,2-a]indole-4,7-dione carbamate 3-(2-cyanoethyl)-1-phenyltriazine was prepared as follows. A solution of 3.2 g of 3-aminopropionitrile fumarate in methanol was treated with 1.35 g of sodium methoxide. The mixture was filtered and the filtrate was concentrated under reduced pressure. The residue was dissolved in 15 ml of N,N-dimethylformamide, treated with excess potassium carbonate, cooled to 0° C., and treated with a solution of 6.25 g of benzenediazonium hexafluorophosphate in 50 ml of N,N-dimethylformamide. After one hour the mixture was poured into ice water and extracted with hexane and ether. The combined extracts were dried and concentrated to an oily residue, which gave 1.2 g of the desired product as yellow needles after crystallization from 500 ml of hexane.

A solution of 3-(2-cyanoethyl)-1-phenyltriazine in 15 ml of dry methylene chloride was added to a solution of 7-hydroxy mitosane (obtained from the hydrolysis of 0.1 g of mitomycin C) in 15 ml of dry methylene chloride. The reaction mixture was stirred at room temperature under nitrogen for 96 hours. The solvent was then evaporated and the residue was purified by preparative thin layer chromatography on silica gel with a mixture of chloroform and methanol 9:1. This procedure gave 21 mg (18%) of the desired compound, having a melting point of 76°–79° C. (decomposition) and showing the following analysis:

NMR (CDCl$_3$,TS) 'δ' values in ppm. The disappearance of the peak at 4.02 and the appearance of new peaks at 2.65–2.80 (t,2) and 4.37–4.5 (t,2).

EXAMPLE 20

1,1a,2,8,8a,8b-Hexahydro-8-(hydroxymethyl)-8a-methoxy-5-methyl-6-[(2-hydroxyethyl)-2-thioethoxy]azirino[2',3':3,4]pyrrolo[1,2-a]indole-4,7-dione carbamate A solution of mitomycin A (100 mg) and 240 mg of 1.6% KOH in excess 2,2'-thiodiethanol was stirred at room temperature under nitrogen for 45 minutes. The reaction mixture was decomposed with dry ice while immersing the flask into a water bath at room temperature. The product was then isolated by chromatography on a silica gel column with elution first by ether containing 6.3% of methanol and then by ether containing 20% methanol. Purification by chromatography on a silica gel plate with CHCl$_3$—MeOH 9:1 gave the title product as a pink solid, which provided the following analysis:

NMR (CDCl$_3$,TS) 'δ' values in ppm.

Disappearance of the singlet at 4.02 and the appearance of new bands at 4.4–4.55 (t,2), 3.7–3.85 (t,2) and 2.65–3.0 (t,4).

EXAMPLE 21

1,1a,2,8,8a,8b-Hexahydro-8-(hydroxymethyl)-8a-methoxy-5-methyl-6-(2,3-dihydroxypropoxy)-azirino[2',3':3,4]pyrrolo[1,2-a]indole-4,7-dione carbamate 3-(2,3-dihydroxypropyl)-1-phenyltriazine was prepared as follows. A cold solution of 10 g of benzenediazonium hexafluorophosphate in 50 ml of N,N-dimethylformamide was added in portions to a solution of 3.6 g of 3-amino-1,2-propanediol in 75 ml of N,N-dimethylformamide at 0° C. After 3 hours the mixture was poured onto ice water and extracted with ether. This extract was dried and concentrated and the residue was treated with boiling hexane.

The insoluble viscous oil was crystallized from chloroform. This procedure gave 1.0 g of the desired triazine as a yellow solid with a melting point of 97°–98° C.

A solution of 7-hydroxymitosane (obtained from the hydrolysis of 0.2 g of mitomycin C) in the minimum volume of methylene chloride was treated with a solution of 0.3 g of 3-(2,3-dihydroxypropyl)-1-phenyltriazine in 200 ml of ether. After 40 hours the insoluble product was collected by filtration, washed with ether, and air dried. This procedure gave 24 mg of the desired compound, which showed the following analysis:

NMR (CDCl$_3$,TS) 'δ' values in ppm. Disappearance of the peak at 4.02 and the appearance of new peaks at 3.3–3.5 (m,5) and 4–4.5 (m,2).

With specific reference to the compounds comprehended by Formula IV, the above examples illustrate the following structural variations.

1. Compounds wherein Z is a mono- or di-hydroxy lower alkoxy radical represented by Examples 10, 12 and 21.
2. Compounds wherein Z is a hydroxy lower alkylthio lower alkoxy radical represented by Example 20.
3. Compounds wherein Z is a halo lower alkoxy radical represented by Example 18.
4. Compounds wherein Z is a cyano lower alkoxy radical represented by Example 19.
5. Compounds wherein Z is a dilower alkoxy lower alkoxy radical represented by Example 15.
6. Compounds wherein Z is a lower alkylamino lower alkoxy radical represented by Example 14.
7. Compounds wherein Z is a hydroxy or lower alkoxy substituted lower alkoxy lower alkoxy radical represented by Examples 4, 13 and 17.
8. Compounds wherein Z is a cyclo lower alkyl substituted lower alkoxy radical represented by Example 3.
9. Compounds wherein Z is a lower alkenyloxy radical represented by Example 1.
10. Compounds wherein Z is a lower alkynyloxy radical represented by Example 2.
11. Compounds wherein Z is a tetrahydro furanyloxy radical or lower alkyl substituted derivative thereof represented by Examples 5 and 11.
12. Compounds wherein Z is a lower alkyl substituted oxiranyloxy radical represented by Example 8.
13. Compounds wherein Z is a lower alkyl substituted dioxolanyloxy radical represented by Example 6.
14. Compounds wherein Z is a lower alkyl substituted pyranyloxy radical represented by Example 7.
15. Compounds wherein Z is a lower alkyl substituted furfuryloxy radical represented by Example 16.
16. Compounds wherein Z is a hydroxy lower alkyl dithio lower alkoxy radical represented by Example 9.

While none of the foregoing examples are illustrative of compounds wherein Y is other than hydrogen, compounds wherein Y is lower alkyl are nonetheless within the comprehension of the invention, reference being made to analogously substituted compounds of my aforesaid U.S. Pat. Nos. 4,268,676 and 4,460,599 and co-pending patent applications Ser. Nos. 264,187 and 464,612.

Compounds according to the present invention are believed to possess anti-bacterial activity against gram-positive and gram-negative microorganisms in a manner similar to that observed for the naturally occurring mitomycins and are thus potentially useful as therapeutic agents in treating bacterial infections in humans and animals.

Usefulness of compounds of Formula IV in the anti-neoplastic therapeutic methods of the invention is demonstrated by the results of in vivo screening procedures wherein the compounds are administered in varying dosage amounts to mice in which a P388 leukemic condition is induced. The procedures were carried out according to "Lymphocytic Leukemia P388-Protocol 1.200", published in *Cancer Chemotherapy Reports*, Part 3, Vol. 3, No. 2, page 9 (September, 1972). Briefly put, the screening procedures involved administration of the test compound to CDF[1] female mice previously infected with 10[6] ascites cells implanted intraperitoneally. Test compounds were administered on the first day of testing only, and the animals were monitored for vitality, inter alia, over a 35-day period.

Results of screening of compounds of Examples 1 through 21 are set forth in Table I below. Data given includes optimal dose ("O.D."), i.e., that dosage in mg/kg of body weight of the animal at which the maximum therapeutic effects are consistently observed. Also included is the maximum survival time ("MST") expressed as the MST of the test animals compared to the MST of controls × 100 ("% T/C"). Within the context of the in vivo P388 procedure noted above, a % T/C value of 125 or greater indicates significant anti-neoplastic therapeutic activity. The lowest dose in mg/kg of body weight at which the 125% T/C value is obtained is known as the minimum effective dose ("MED"). These doses also are listed in Table I. It is worthy of note that the exceptionally high MST values obtained in the P388 screenings reported in Table I are also indicative of the absence of substantial toxicity of the compounds at the dosages indicated.

TABLE I

| Example No. | Optimal Dose mg/kg | MST as % T/C | MED |
|---|---|---|---|
| 1 | 1.6 | 156 | 0.1 |
| 2 | 0.8 | 150 | <0.05 |
| 3 | 1.6 | 144 | 0.4 |
| 4 | 1.6 | 167 | <0.01 |
| 5 | 0.8 | 239 | <0.05 |
| 6 | 0.8 | 178 | <0.05 |
| 7 | 0.8 | 161 | 0.1 |
| 8 | 1.6 | 129 | 1.6 |
| 9 | 1.6 | 259 | <0.025 |
| 10 | 0.8 | 300 | <0.0125 |
| 11 | 3.2 | 178 | <0.05 |
| 12 | 1.6 | 175 | 0.05 |
| 13 | 0.4 | 210 | 0.1 |
| 14 | 3.2 | 281 | <0.025 |
| 15 | 1.6 | 200 | <0.1 |
| 16 | 3.2 | 150 | 0.2 |
| 17 | 0.4 | 200 | 0.05 |

TABLE I-continued

| Example No. | Optimal Dose mg/kg | MST as % T/C | MED |
|---|---|---|---|
| 18 | 1.6 | 269 | <0.025 |
| 19 | 6.4 | 139 | 6.4 |
| 20 | 3.2 | 240 | <0.1 |
| 21 | 12.8 | 225 | 0.2 |

Clearly among the most preferred compounds employed as antineoplastic agents according to the invention are those exhibiting more than twice the relative life-extending capacity generally characterized as evidencing significant therapeutic potential, i.e., those having an MST % T/C value greater than 2×125. The class of such compounds is seen to include the compounds of Examples 9, 10, 14 and 18.

As may be noted from Table I, initial single dosages of as little as 0.4 mg/kg showed substantial long term antineoplastic activity. Accordingly, the methods of the invention may involve therapeutic administration of unit dosages of as little as 0.001 mg or as much as 5 mg, preferably from 0.004 mg to 10 mg, of the compounds as the active ingredient in a suitable pharmaceutical preparation. Such preparations may be administered in a daily regimen calling for from 0.1 mg to 100 mg per kg., preferably from about 0.2 to about 51.2 mg per kg, of the body weight of the animal suffering from neoplastic disease. It is preferred that the compounds be administered parenterally. Pharmaceutical compositions suitable for use in practice of methods of the invention may comprise simple water solutions of one or more of the compounds of Formula IV, but may also include well known pharmaceutically acceptable diluents, adjuvants and/or carriers such as saline suitable for medicinal use.

Further aspects and advantages of the present invention are expected to occur to those skilled in the art upon consideration of the foregoing description and consequently only such limitations as appear in the appended claims should be placed thereon.

What is claimed is:

1. Compounds of the formula,

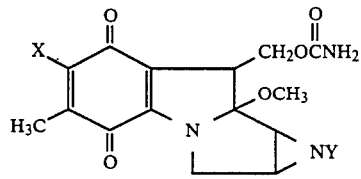

wherein: Y is hydrogen, or lower alkyl; and X is a group of the formula —O—R, wherein R is di-lower alkoxy lower alkyl.

2. A method for treatment of a neoplastic disease state in an animal, said method comprising administering to an animal having such a disease a therapeutically effective amount of a compound of the formula,

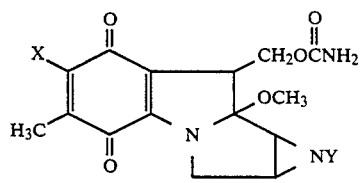

wherein: Y is hydrogen, or lower alkyl; and X is a group of the formula —O—R, wherein R is di-lower alkoxy lower alkyl.

3. A pharmaceutical composition for use in treatment of a neoplastic disease in an animal, said composition comprising a pharmaceutically acceptable solvent, diluent, adjuvant or carrier and, as the active ingredient, from about 0.4 mg. to about 12.8 mg. of a compound of the formula,

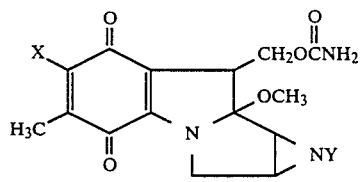

wherein: y is hydrogen, or lower alkyl; and X is a group of the formula —O—R, wherein R is di-lower alkoxy lower alkyl.

* * * * *

UNITED STATES PATENT AND TRADEMARK OFFICE
CERTIFICATE OF CORRECTION

PATENT NO. : 4,888,341

DATED : December 19, 1989

INVENTOR(S) : William A. Remers, et al

It is certified that error appears in the above-identified patent and that said Letters Patent is hereby corrected as shown below:

Col. 1, line 9, after "U.S." should be --Letters--.

Col. 2, line 49, "-C-R" should be -- -N-R --.

Signed and Sealed this

Twenty-second Day of December, 1992

*Attest:*

DOUGLAS B. COMER

*Attesting Officer*     *Acting Commissioner of Patents and Trademarks*